United States Patent [19]
Zickel

[11] 4,289,124
[45] Sep. 15, 1981

[54] SURGICAL APPLIANCE FOR THE FIXATION OF FRACTURED BONES

[76] Inventor: Robert E. Zickel, 75 Villard Ave., Hastings-on-Hudson, N.Y. 10706

[21] Appl. No.: 943,213

[22] Filed: Sep. 18, 1978

[51] Int. Cl.³ .............................................. A61F 5/04
[52] U.S. Cl. ................................................ 128/92 D
[58] Field of Search ............... 128/92 R, 92 A-92 E, 128/92 G, 334 R, 334 C, 335

[56] References Cited
U.S. PATENT DOCUMENTS

| 583,455 | 3/1897 | Bush | 128/92 D |
|---|---|---|---|
| 1,201,864 | 9/1916 | Overmeyer | 128/92 R |
| 2,110,414 | 2/1938 | Bell | 128/92 D |
| 2,439,995 | 7/1948 | Thrailkill | 128/92 BA |
| 3,680,553 | 8/1972 | Seppo | 128/92 BC |
| 3,807,394 | 4/1974 | Attenborough | 128/92 B |
| 3,862,631 | 1/1975 | Austin | 128/92 B |
| 3,900,025 | 8/1975 | Barnes, Jr. | 128/92 D |
| 4,187,841 | 2/1980 | Knutson | 128/92 E |

FOREIGN PATENT DOCUMENTS

| 417110 | 3/1924 | Fed. Rep. of Germany | 128/336 |
|---|---|---|---|
| 2213283 | 8/1973 | Fed. Rep. of Germany | 128/92BA |
| 2649042 | 5/1978 | Fed. Rep. of Germany | 128/92 B |
| 1051847 | 6/1954 | France | 128/92 D |
| 167008 | 3/1963 | U.S.S.R. | 128/92 R |
| 214020 | 5/1968 | U.S.S.R. | 128/92 R |

Primary Examiner—Robert W. Michell
Assistant Examiner—C. W. Shedd
Attorney, Agent, or Firm—Curtis, Morris & Safford

[57] ABSTRACT

A surgical appliance for the fixation of fractured bones includes two anchoring members each adapted to be imbedded into a respective segment of a fractured bone. Each anchoring member has a head portion which extends from the bone, the head portion including a channel therethrough to receive a bolt. In one embodiment, one of the channels is threaded. The bolt, which is formed of a shaft and a head, has at least a portion of the shaft provided with screw threads which mate with the threads of the one channel. The shaft of the bolt is adapted to pass through the channel of the first anchoring member and to be threadedly received in the channel of the second anchoring member so as to exert a compressional force on the segment of the fractured bone when the bolt is tightened. In another embodiment, the channels of both heads of the anchoring members are provided with screw threads.

3 Claims, 4 Drawing Figures

SURGICAL APPLIANCE FOR THE FIXATION OF FRACTURED BONES

BACKGROUND OF THE INVENTION

This invention relates to a surgical appliance for the fixation of fractured bones and, more particularly, to an extramedullary surgical appliance which, when in use, exerts a desirable compressional force on the segments of the fractured bone.

Various devices are known for use in setting fractured bones. One type of device is described in U.S. Pat. Nos. 3,374,786 and 3,996,931, both issued to G. R. Callender. This device is particularly adapted for the fixation of fractured bone segments in a femur. A trochanteric plate is secured to the upper segment of the femur by means of surgical screws, this plate being provided with a sleeve member attached thereto at an appropriate angle. The upper segment of the femur is bored to receive the sleeve member and also to receive an elongated shaft having a screw portion, which shaft is embedded within the femoral head by means of the surgical screw portion. An adjustable limit screw assembly serves to retain the shaft member within the sleeve member. The sleeve member carries a key which is insertable into grooves of different lengths on the shaft member, depending upon the type of fixation which is desired. Axial compression is provided by adjusting the limit screw assembly.

Unfortunately, the device of the type described in the aforementioned Callender patents is limited solely for use in the fixation of a femur. Because of the particular angular displacement of the sleeve member relative to the plate member on which it is formed, this device cannot be used in other bones, particularly the humerus bone. Also, the device described in the Callender patents is relatively complex and, accordingly, is accompanied by relatively high manufacturing costs. Still further, it is somewhat difficult to use. Moreover, since the throchanteric plate and the shaft member must be embedded into the femur, it is difficult to use this device in combination with other, conventional fixation devices, such as surgical pins or screws, in the event of a three-part fracture, or other multiple fracture, of the femur.

Another type of surgical appliance which has been proposed for the fixation of fractures is described in U.S. Pat. No. 1,997,466, issued to E. E. Longfellow. This device consists of a pair of skeletal pins which are inserted through the bone on either side of the fracture, which pins extend from the injured limb. Turnbuckles are secured to opposite ends of the pair of pins and are suitably tightened so as to exert a compressional force on the fracture. However, since the pins extend externally of the injured limb, and since the turnbuckles must be secured at the extreme outward ends of such pins, there is the danger of infection. Also, in the event of an inadvertent blow or force imparted to the turnbuckle assembly, the injured limb can be further damaged. Still further, the overall appliance is relatively bulky and unwieldy for the patient, thus adding to his discomfort. In addition, the device is not easily usable by the surgeon.

A device which has been proposed for correcting certain forms of physical deformity by exerting compressional forces onto selected vertebrae is described in U.S. Pat. No. 3,997,138, issued to H. V. Crock et al. In this device, a pair of surgical screws are embedded into the vertebrae. Each screw includes a head containing channels through which rods are passed. A caliper, formed of a pair of levers, is used to urge the surgical screws, which are embedded into the vertebrae, either closer together or farther apart. When the proper relative position of these screws is attained, the rods which link the screws are clamped thereto, and then the caliper is removed. Thus, the position of the screws, and thus the vertebrae, is fixed.

While this device might be suitable for correcting certain physical deformities, the fact that a caliper is required to position the surgical screws results in a complicated procedure whereby the device is not suited for the fixation of fractures. Furthermore, the caliper which must be used with the surgical screws is quite expensive, in and of itself.

Accordingly, there is a need for a surgical device for the fixation of fractured bones which is relatively simple to manufacture and to use, yet which is adapted to exert desirable compressional forces on the fracture. Also, there is a need for such a surgical device which can be used in conjunction with other fixation devices, such as other intramedullary devices, or can be used with extramedullary devices.

OBJECTS OF THE INVENTION

Therefore, it is an object of the present invention to provide an improved surgical appliance for the fixation of fractured bones which overcomes the aforenoted disadvantages of the prior art and, moreover, which satisfies the aforenoted need.

Another object of this invention is to provide an extramedullary appliance for the fixation of fractured bones and, particularly, for the fixation of the humerus bone.

A further object of this invention is to provide an improved surgical applicance which can be used in the fixation of a multi-part fracture wherein intramedullary pins or screws can be used to fix some of the parts and wherein the improved appliance can be used to fix the remaining part or parts, and particularly small bone fragments.

An additional object of this invention is to provide an improved surgical appliance which is readily adapted for the fixation of fractures in the supracondylar and intracondylar regions of the humerus bone.

Yet another object of this invention is to provide an improved surgical device for the fixation of fractured bones, which device is of relatively simple construction and which can be used easily and quickly by a surgeon.

Various other objects, advantages and features of the present invention will become readily apparent from the ensuing detailed description, and the novel features will be particularly pointed out in the appended claims.

SUMMARY OF THE INVENTION

In accordance with this invention, a surgical appliance is provided for the fixation of fractured bones. The appliance includes a pair of anchoring members, each adapted to be embedded into a respective segment of a fractured bone, and each member having a head portion which extends from its segment and which includes a channel therethrough for receiving a bolt. At least one of the channels through the head portions of the anchoring members is threaded. The bolt, which is adapted to pass through the channels of the anchoring members, is provided with screw threads on at least a portion of its shaft, which screw threads mate with the threads of the one channel. Thus, the bolt is threadedly received in the channel of the appropriate anchoring member so that, when the bolt is tightened, a compressional force is exerted on the two anchoring members, thereby exerting a compressional force on the segments of the fractured bone. In one embodiment, one of the channels is smooth so as to slidably receive the bolt. In another embodiment, both channels of the anchoring members are threaded so that the bolt is screwed into both anchoring members.

BRIEF DESCRIPTION OF THE DRAWINGS

The following detailed description, given by way of example, will best be understood in conjunction with the accompanying drawings in which.

DETAILED DESCRIPTION OF A PREFERRED EMBODIMENT

Figure 1:
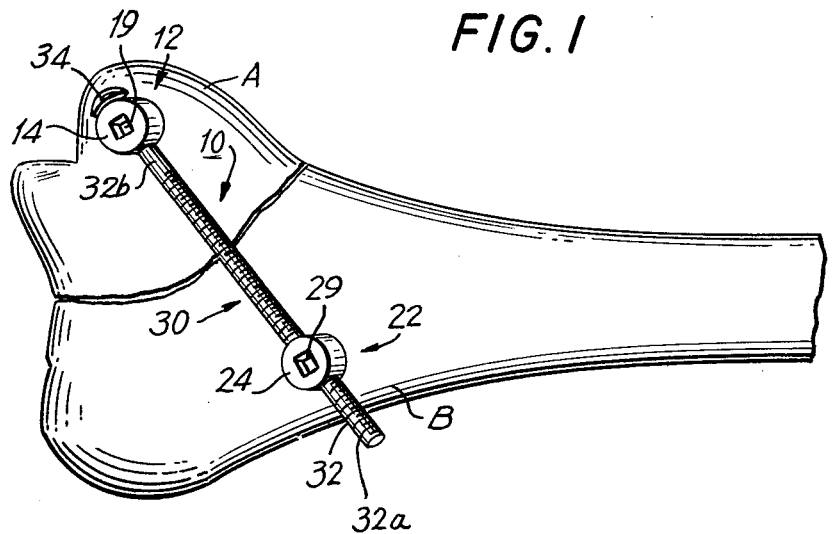
FIG. 1 is a perspective view of one embodiment of the present invention, and illustrates the use of this invention.

Referring now to the drawings, wherein like reference numerals are used throughout, there is illustrated one embodiment of a surgical appliance 10 in accordance with the present invention. FIG. 1 illustrates the use of appliance 10 for the fixation of a fracture in the condyle at the distal end of the humerus bone. As is known, fractures in the supracondylar and intracondylar regions of the humerus bone present a particular problem in the fixation thereof. This is because of the anatomical configuration of the condyle. That is, because of the very narrow medullary canal of the bone, it is difficult to use intramedullary appliances. Furthermore, because a fracture of this region of the humerus bone generally results in one or more small fragments, an extramedullary fixation device, such as a plate, cannot be used easily with such small fragments.

Figure 2:
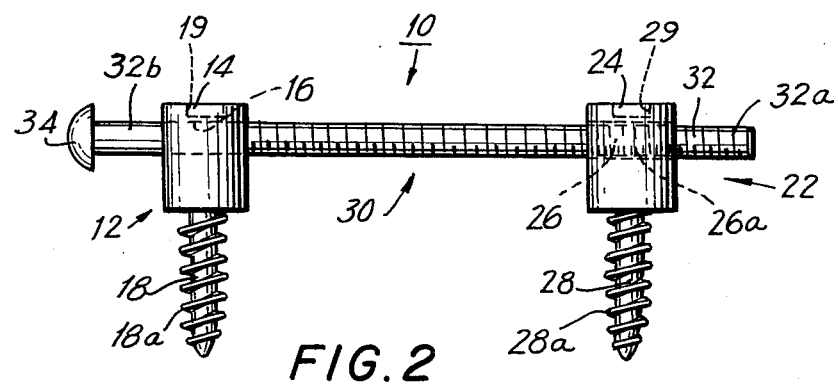
FIG. 2 is a plan view of an embodiment of this invention.
Figure 3:
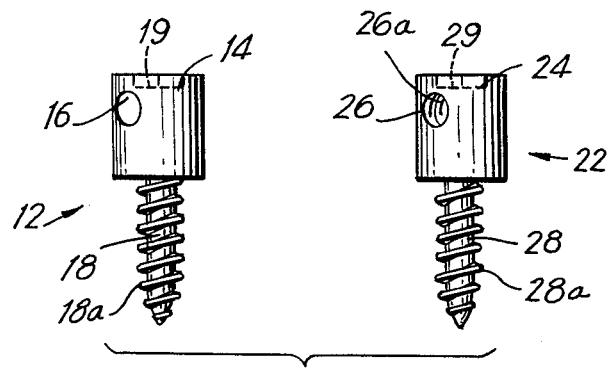
FIG. 3 and FIG. 4 are perspective views of the anchoring members in accordance with two embodiments of this invention.
Figure 4:
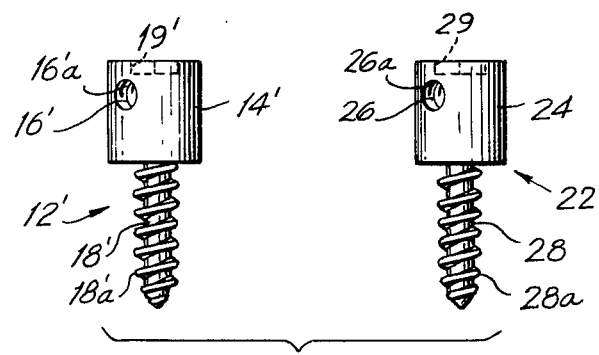

These problems are solved by appliance 10 which is illustrated as being used for the fixation of the fracture between segments A and B of the illustrated bone. As shown in FIGS. 1-3, device 10 is comprised of a pair of anchoring members 12 and 22, these members being formed of head portions 14 and 24 from which extend shafts 18 and 28, respectively. These shafts are provided with screw threads 18a and 28a. Preferably, each anchoring member is of unitary construction and is formed of surgical steel, titanium or other conventional material normally used in surgically implanted devices. Head portion 14 of anchoring member 12 is provided with a channel 16 therethrough. In the illustrated embodiment, channel 16 is smooth. Head portion 24 of anchoring member 22 is provided with a channel 26 therethrough. As shown more clearly in FIGS. 2 and 3, channel 26 is threaded, as represented by screw thread 26a.

A bolt 30, having a head portion 34 and a shaft 32, is provided. At least a portion of shaft 32 is provided with screw threads 32a, these threads mating with screw threads 26a provided in channel 26 in head portion 24 of anchoring member 22. In FIGS. 1 and 2, a portion 32b of shaft 32 is free of screw threads. However, in an alternative embodiment, screw threads are provided along the entire length of shaft 32.

Preferably, the axis of each of channels 16 and 26 is perpendicular to the longitudinal axis of shafts 18 and 28, respectively. Thus, when used, shaft 32 passes through channels 16 and 26 and is disposed substantially perpendicular to the threaded shafts of each of the anchoring members. Of course, if desired, any other geometric or angular relationship between shaft 32 and shafts 18 and 28 may be selected.

The top surface of each of head portions 14 and 24 of anchoring members 12 and 22 is adapted to receive an insertion tool (not shown) whereby the anchoring member can be suitably rotated and thus screwed into a respective segment of the fractured bone. In FIG. 1, the top surface of each of head portions 14 and 24 is provided with a square-shaped receptacle 19 and 29, adapted to receive a socket-type insertion device. Alternatively, the head portion of each anchoring member may be provided with a suitable slot into which a screw driver can be inserted. Still further, head portion 14, as well as head portion 24, may be suitably shaped, such as square-shaped, so that a socket-type screw driver may be placed thereover and rotated so as to drive the respective anchoring members into the respective segments of the fractured bone.

In operation, anchoring member 12 is screwed into segment A such that its threaded shaft 18 is embedded into the bone segment. Then, anchoring member 22 is inserted into segment B. As mentioned above, any conventional insertion tool can be used to insert the respective anchoring members into segments A and B. Of course, head portion 14 extends upward from segment A, and head portion 24 likewise extends upward from segment B. Channels 16 and 26 of anchoring members 12 and 22 are aligned with each other. Then, shaft 32 is inserted into and passes through smooth channel 16. When threaded portion 32a of shaft 32 extends to channel 26, bolt 30 is rotated such that the bolt is screwed into this channel. That is, screw threads 26a of channel 26 threadedly engage screw threads 32a of bolt 30. In this regard, head 34 of bolt 30 may be provided with a slot or other suitable device for receiving a suitable tool which facilitates the rotation of the bolt.

As bolt 30 is tightened further, it is appreciated that head 34 soon will abut against head portion 14 of anchoring member 12, as shown in FIG. 1. Then, any further tightening of the bolt exerts a compressional force on the anchoring members, thus exerting a corresponding compressional force on segments A and B. It is appreciated that this compressional force is urged along the length of shaft 32 of bolt 30. The amount of compressional force is, of course, dependent upon the amount by which the bolt is tightened into channel 26 of anchoring member 22. Since mating screw threads are provided between this channel and shaft 32 of the bolt, this compressional force can be made to vary substantially continuously as a function of the degree of tightening.

In the illustrated embodiment, channel 16 in head portion 14 of anchoring member 12 is free of screw threads. In an alternative embodiment, this channel may be provided with screw threads (not shown), similar to threaded channel 26. When using this alternative embodiment, bolt 30 first is screwed into and through channel 16 until threaded portion 32a is received by channel 26 of the other anchoring member. Then, continued rotation of bolt 30 urges head 34 thereof toward head portion 14. When head 34 abuts against head portion 14, further tightening of bolt 30 exerts a compressional force on the two anchoring members, and thus on segments A and B, as in the above-described embodiment. Thus, a desired, precise compressional force can be exerted on these fractured bone segments.

As yet another alternative embodiment, shaft 32 of bolt 30 may be provided with screw threads 32a along its entire length. That is, head 34 may be secured directly to one end of the threaded shaft of bolt 30, and need not necessarily be separated therefrom by smooth portion 32b, as illustrated in FIGS. 1 and 2. Regardless of whether shaft 32 is threaded along its entire length or over only a portion of that length, bolt 30 cooperates with anchoring members 12 and 22 in substantially the same manner.

The entire surgical appliance, comprised of anchoring members 12 and 22 and bolt 30, is intended for internal use. That is, the entire device is disposed beneath the skin and muscle of the limb (e.g. the arm) to which it is secured. Depending upon the thicknesses of the particular bone of the patient with which this device is used, shafts 18 and 28 may be of any desirable lengths. Preferably, various different length shafts will be provided so as to accommodate bones of different thicknesses. Similarly, head portions 14 and 24 may be of different diameters. Likewise, the length and diameter of bolt 30 may be manufactured in a variety of sizes so as to be readily adapted for different situations. As may be appreciated, depending upon the fracture site, anchoring members 12 and 22 may be separated from each other by a relatively large distance, thus requiring a bolt having a relatively long shaft length. In other fractures, when the anchoring members are suitably embedded into segments A and B, such anchoring members may be separated by a relatively short distance. Hence, the bolt which is to be used therewith preferably should be of a relatively short length.

It also is contemplated that, in order to facilitate the alignment of channels 16 and 26 for the passage of shaft 32 of bolt 30 therethrough, head portions 14 and 24 each may be rotatable with respect to shafts 18 and 28, respectively, by, for example, an amount limited to 180°. Such partial rotation of the respective head portions will permit the respective channels to be aligned, yet will also enable a suitable tool to be used for the insertion and subsequent withdrawal of the anchoring members. That is, by limiting the rotational movement of the head portion of each anchoring member, a screw driver, insertion drill or the like still can be used to rotate the entire anchoring member, and thus screw that member into the bone segment. Nevertheless, this will not present an undesirable impediment against the exertion of compressional forces on the anchoring members once they are inserted into the fractured bone segments.

It may be appreciated that the device shown and described herein can be used for the fixation of almost any fracture and need not be limited solely for use in the fixation of the condyle of the humerus bone. This extramedullary device is particularly advantageous for use in fixing small fragments which cannot be fixed easily by the use of conventional appliances, such as plates. Thus, the present invention can be used in cooperation with other conventional fixation appliances, such as pins or screws. For example, in a three-part fracture, it is possible that two of the fragments could be fixed by use of intradmedullary pins which, of course, are inserted into the medullary canal. However, as is common, by using such intramedullary pins, there may be insufficient space for yet a third pin. Nevertheless, by providing the device of the present invention, the third fragment can be suitably fixed with proper compression exerted thereon. That is, anchoring member 12, as shown and described herein, can be embedded into the third fragment, and anchoring member 22 can be embedded into the main portion of the fractured bone.

While the present invention has been particularly shown and described with reference to certain preferred embodiments, it should be appreciated that various changes and modifications in form and details can be made without departing from the spirit and scope of the invention. It is, therefore, intended that the appended claims be interpreted as including all such changes and modifications.

What is claimed is:

1. A surgical appliance for the fixation of fractured bones, comprising a first anchoring member having a threaded shaft adapted to be embedded into one segment of a fractured bone, said first anchoring member having a substantially cylindrical head portion extending from said threaded shaft and including a channel therethrough for receiving a bolt; a second anchoring member having a threaded shaft adapted to be embedded into another segment of said fractured bone, said second anchoring member having a substantially cylindrical head portion extending from said second-mentioned threaded shaft and including a channel therethrough for receiving said bolt, one of said channels being threaded, each of said substantially cylindrical head portions further including a receptacle therein for receiving an insertion tool which, when rotated, drives the threaded shaft of the respective anchoring member into said respective segment of said fractured bone; and a bolt having a shaft and a head, at least a portion of said shaft being provided with screw threads which mate with the threads of said one channel, the shaft of said bolt being adapted to pass through the channel of said first anchoring member and to be threadedly received in the channel of said second anchoring member such that said shaft, when received by both channels of the cylindrical head portions of said anchoring members, extends substantially perpendicular to the threaded shafts of each of said anchoring members, so as to exert a compressional force on said one and other segments of said fractured bone when said bolt is tightened.

2. The surgical appliance of claim 1 wherein the channel of said first anchoring member is free of screw threads so as to slidably receive the shaft of said bolt, whereby the head of said bolt is adapted to abut against the head of said first anchoring member when said bolt is in operative position with respect to said first and second anchoring members.

3. The surgical appliance of claim 1 wherein the channels of both said first and second anchoring members are threaded to receive the screw threads of the shaft of said bolt.

* * * * *